(12) United States Patent
Tanji (10) Patent No.: US 6,409,715 B1
(45) Date of Patent: Jun. 25, 2002

(54) DISPOSABLE ABSORBENT ARTICLE

(75) Inventor: Hiroyuki Tanji, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 17 days.

(21) Appl. No.: 09/589,079

(22) Filed: Jun. 8, 2000

(30) Foreign Application Priority Data

Jun. 9, 1999 (JP) ............................................. 11-163025

(51) Int. Cl.[7] ................................................. A61F 13/15
(52) U.S. Cl. ............................ 604/385.19; 604/385.01; 604/385.16; 604/385.201
(58) Field of Search ..................... 604/385.01, 385.101, 604/385.03, 385.04, 385.06, 385.07, 385.12, 385.22, 385.23, 385.19, 385.16, 385.201

(56) References Cited

U.S. PATENT DOCUMENTS 3,561,446 A * 2/1971 Jones .......................... 128/287
6,183,587 B1 * 2/2001 McFall et al. ............... 156/201
6,284,942 B1 * 9/2001 Rabin .......................... 604/361
6,287,288 B1 * 9/2001 Osborn, III et al. ..... 604/385.04

FOREIGN PATENT DOCUMENTS

| JP | 5-86320 | 11/1993 |
| JP | 6-5614 | 1/1994 |
| JP | 6-21624 | 3/1994 |
| JP | 8-191857 | 7/1996 |
| JP | 8-196565 | 8/1996 |

\* cited by examiner

Primary Examiner—John G. Weiss
Assistant Examiner—Michael Bogart
(74) Attorney, Agent, or Firm—Clark & Brody (57) ABSTRACT

A disposable absorbent article including a liquid-permeable topsheet, which is provided at a desired location of upper and lower surfaces with a stretchable region adapted to be stretchable up- and downward with respect to the upper and lower surface, the region being formed by a plurality of pleats.

10 Claims, 7 Drawing Sheets

DISPOSABLE ABSORBENT ARTICLE

BACKGROUND OF THE INVENTION

This invention relates disposable absorbent article such as disposable diapers or menstruation pads.

As a liquid-pervious sheet conventionally used in body fluids absorbent article, it is well known to use a nonwoven fabric or porous plastic film partially formed with a plurality of crests and troughs alternately arranged in one direction to shape stretchable bellows or a composite sheet comprising a nonwoven fabric and elastic members secured under tension to the nonwoven fabric to make the composite sheet elastic.

The region of the sheet shaped in bellows has an elasticity in one direction and forms a groove which is concave either in one direction or in the opposite direction depending on the direction in which the region shaped in bellows is depressed. However, it is impossible for such sheet to be stretched in all directions, i.e., a stretchable concave or convex different from the groove can not be formed in a desired region of the sheet.

The composite sheet comprising the nonwoven fabric and the elastic members secured under tension to the nonwoven fabric inevitably generates a plurality of fine gathers which may give the wearer a feeling of discomfort as the gathers come in contact with the wearer's skin.

SUMMARY OF THE INVENTION

It is an object of this invention to provide disposable absorbent article including a liquid-pervious topsheet having an elastically stretchable region adapted to form a concave or convex in a predetermined zone without giving the wearer a feeling of discomfort.

According to this invention, there is provided a disposable absorbent article comprising: a liquid-permeable topsheet; a liquid-impermeable backsheet; a liquid-absorbent core disposed therebetween; and the topsheet being provided at a predetermined location on upper and lower surface thereof with a stretchable region adapted to be stretchable up- and downward with respect to the upper and lower surfaces, the stretchable region being formed by a plurality of pleats undulating from a peripheral edge toward a central zone of the stretchable region.

DETAILED DESCRIPTION OF THE PREFERRED EMBODIMENTS

Figure 1:
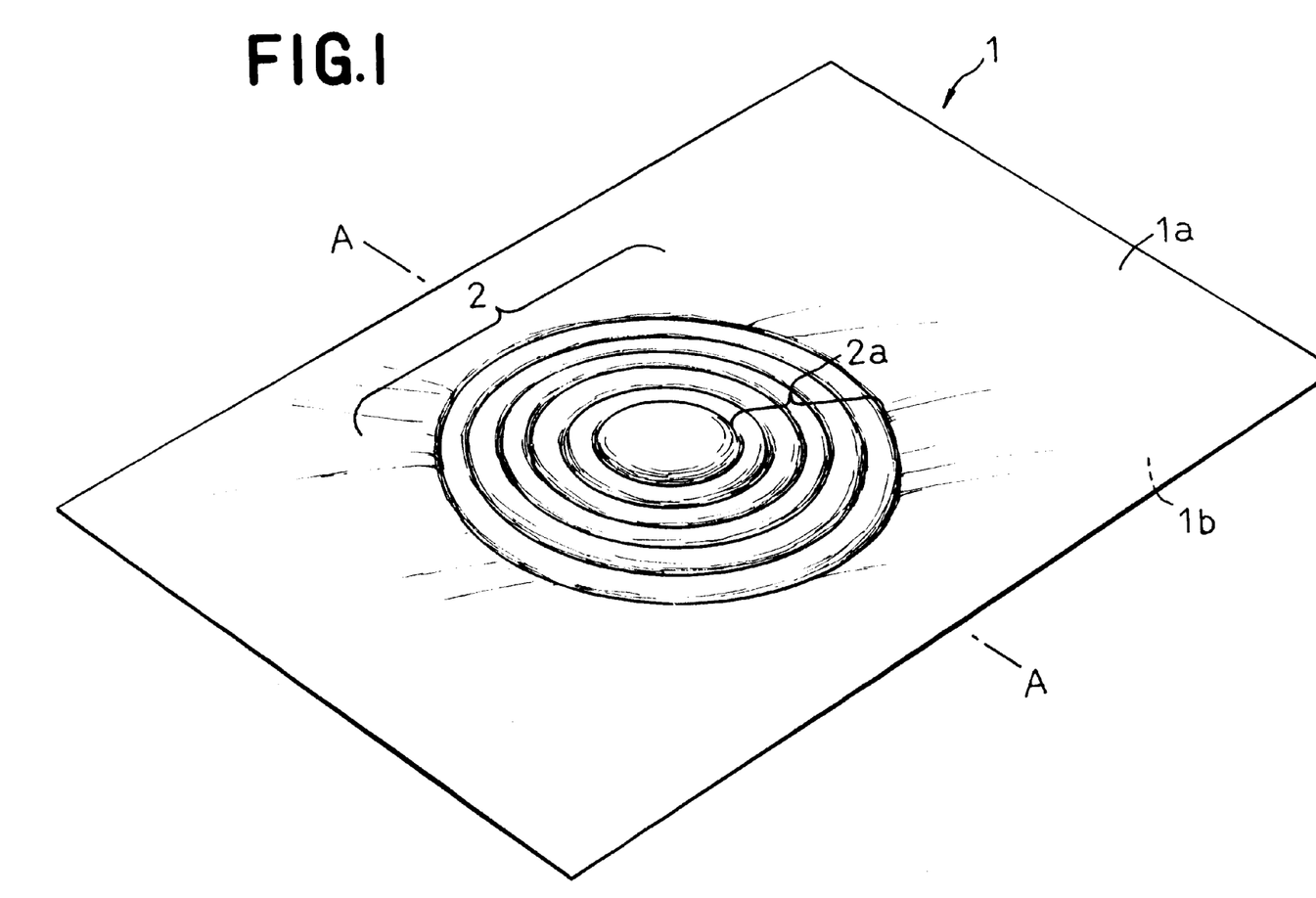
FIG. 1 is a perspective view showing a liquid-pervious topsheet provided in accordance with one embodiment of this invention.
Figure 2:
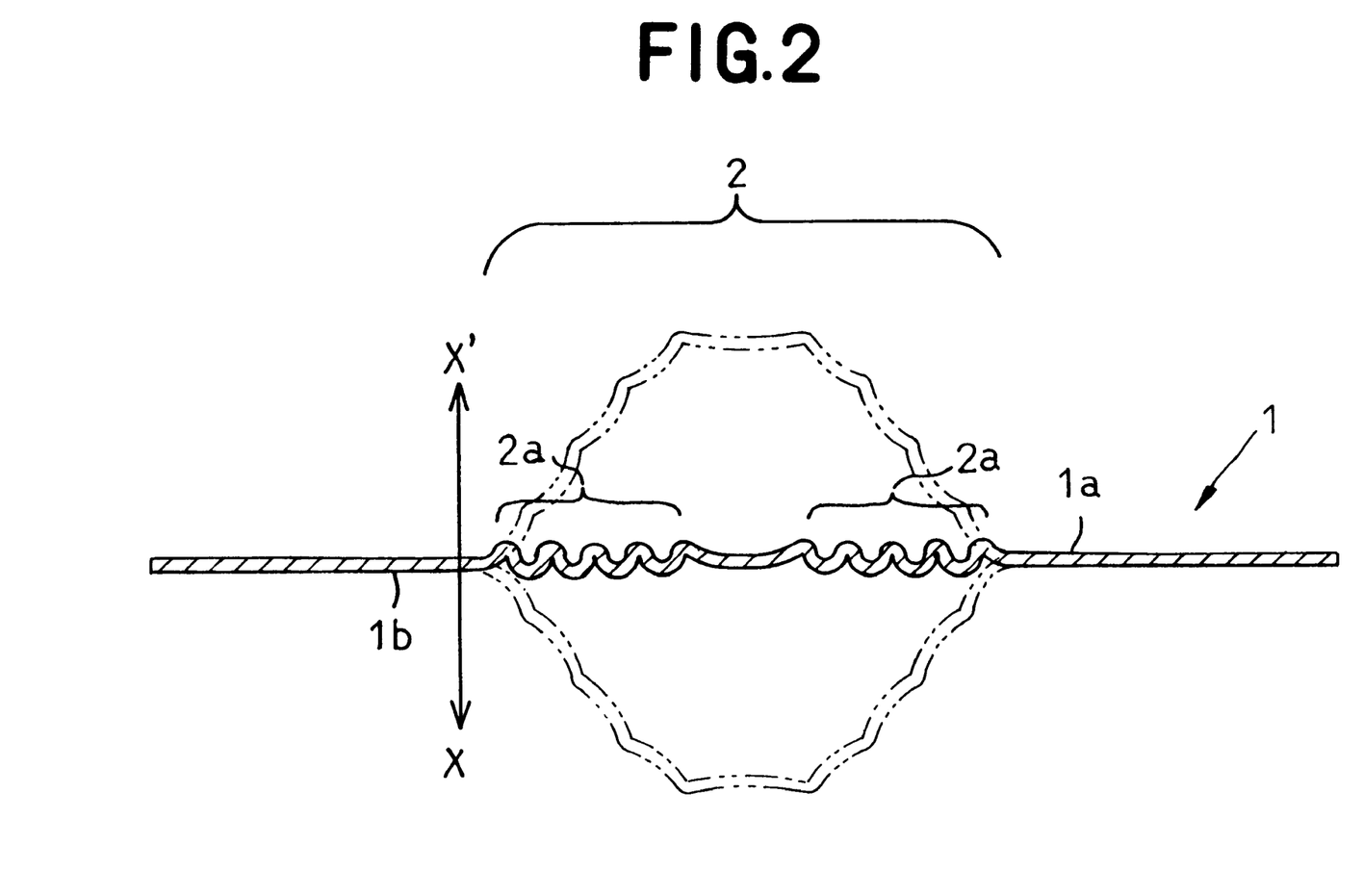
FIG. 2 is a sectional view taken along line A—A in FIG. 1.

FIG. 1 is a perspective view showing a liquid-pervious topsheet 1 provided in accordance with one embodiment of this invention and FIG. 2 is a sectional view taken along line A—A in FIG. 1. Referring to FIG. 2, imaginary lines indicate a stretchable region 2 of the topsheet 1 as being stretched up- and downward. The topsheet 1 is flexible and made of a liquid-pervious nonwoven fabric formed by thermoplastic synthetic resin fiber. The topsheet 1 has upper and lower surfaces 1a, 1b and is formed in the vicinity of its central location with the stretchable region 2 adapted to be stretchable or deformable up- and downward with respect to the upper and lower surfaces 1a, 1b. The stretchable region 2 comprises a plurality of circular pleats 2a undulating from a peripheral edge of the stretchable region 2 toward a center of the stretchable region 2. In the stretchable region 2, the plurality of circular pleats 2a are coaxially arranged with their circumferences progressively reduced toward the center of the stretchable region 2.

The topsheet 1 is stretchable or deformable up- and downward with respect to the upper and lower surfaces 1a, 1b as indicated by a double-headed arrow X—X so as to form the topsheet 1 with a concave or a convex as the pleats 2a are stretched or deformed.

Figure 3:
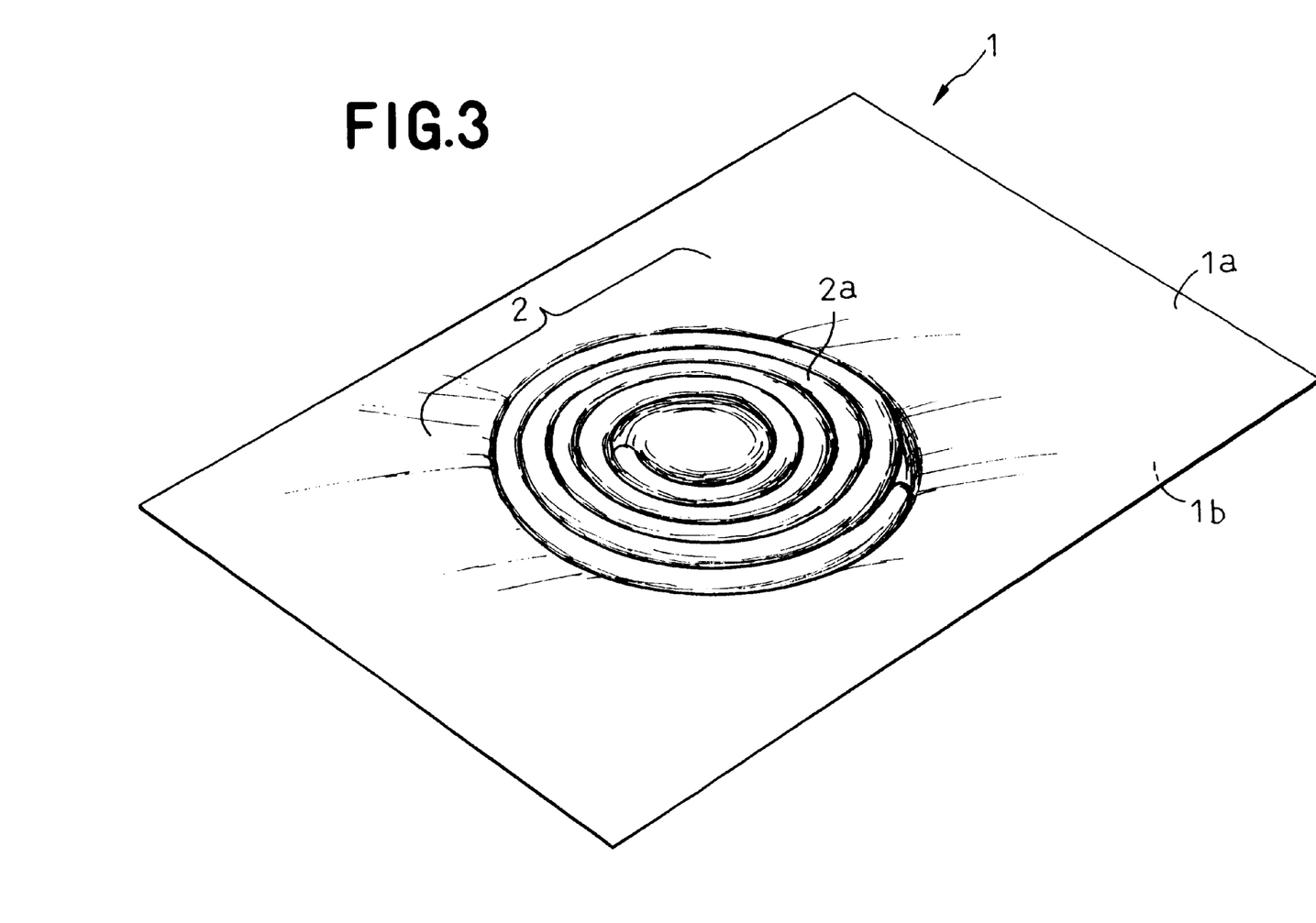
FIG. 3 is a view similar to FIG. 1 but showing another embodiment of the liquid-pervious topsheet.

FIG. 3 is a view similar to FIG. 1 but showing another embodiment of the liquid-pervious topsheet 1. The topsheet 1 according to this embodiment is similar to the topsheet 1 of FIG. 1 in that this topsheet 1 also is made of a liquid-pervious nonwoven fabric formed by thermoplastic synthetic resin fiber and has the stretchable region 2 adapted to be stretchable or deformable up- and downward with respect to the upper and lower surfaces 1a, 1b. As will be apparent from FIG. 3, the topsheet 1 according to this embodiment differs from the topsheet 1 of FIG. 1 in that the stretchable region 2 is formed by a spiral pleat 2a so as to undulate from the peripheral edge of the stretchable region 2 toward the center of the stretchable region 2.

In the case of the topsheet 1 shown by FIGS. 1 and 3, it is possible to form the upper and lower surfaces 1a, 1b with the stretchable region 2 in a location other than the central location or even to form the upper and lower surfaces 1a, 1b with a plurality of such stretchable regions 2.

The topsheet 1 is made of a hydrophobic nonwoven fabric treated to become hydrophilic or a hydrophilic nonwoven fabric formed by hydrophiling agent rubbed in fiber. It is also possible to use a porous thermoplastic synthetic resin film in the place of such a nonwoven fabric to form the topsheet 1. The nonwoven fabric is preferably selected from a group including an air-through nonwoven fabric, a point bond nonwoven fabric and a spun bond nonwoven fabric.

Figure 4:
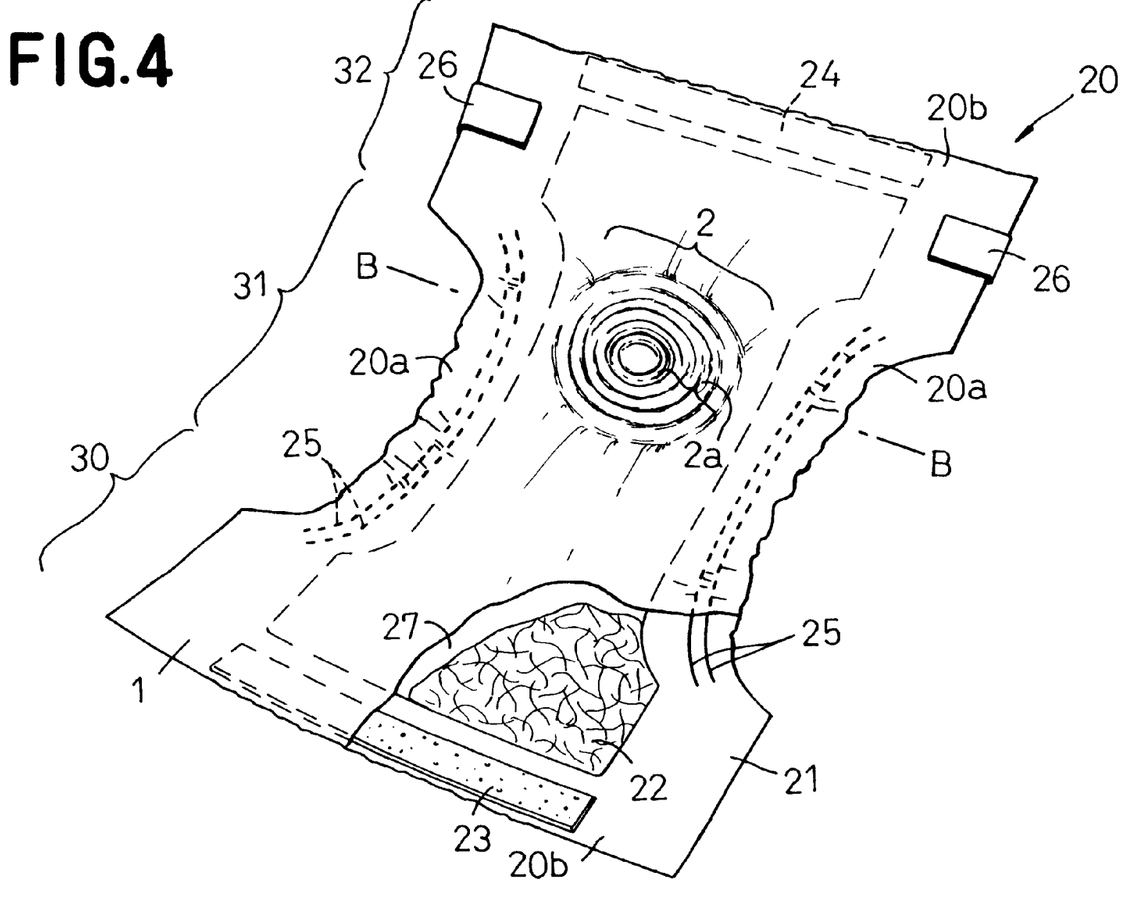
FIG. 4 is a perspective view showing a disposable diaper using the sheet of FIG. 1 as partially broken away.
Figure 5:
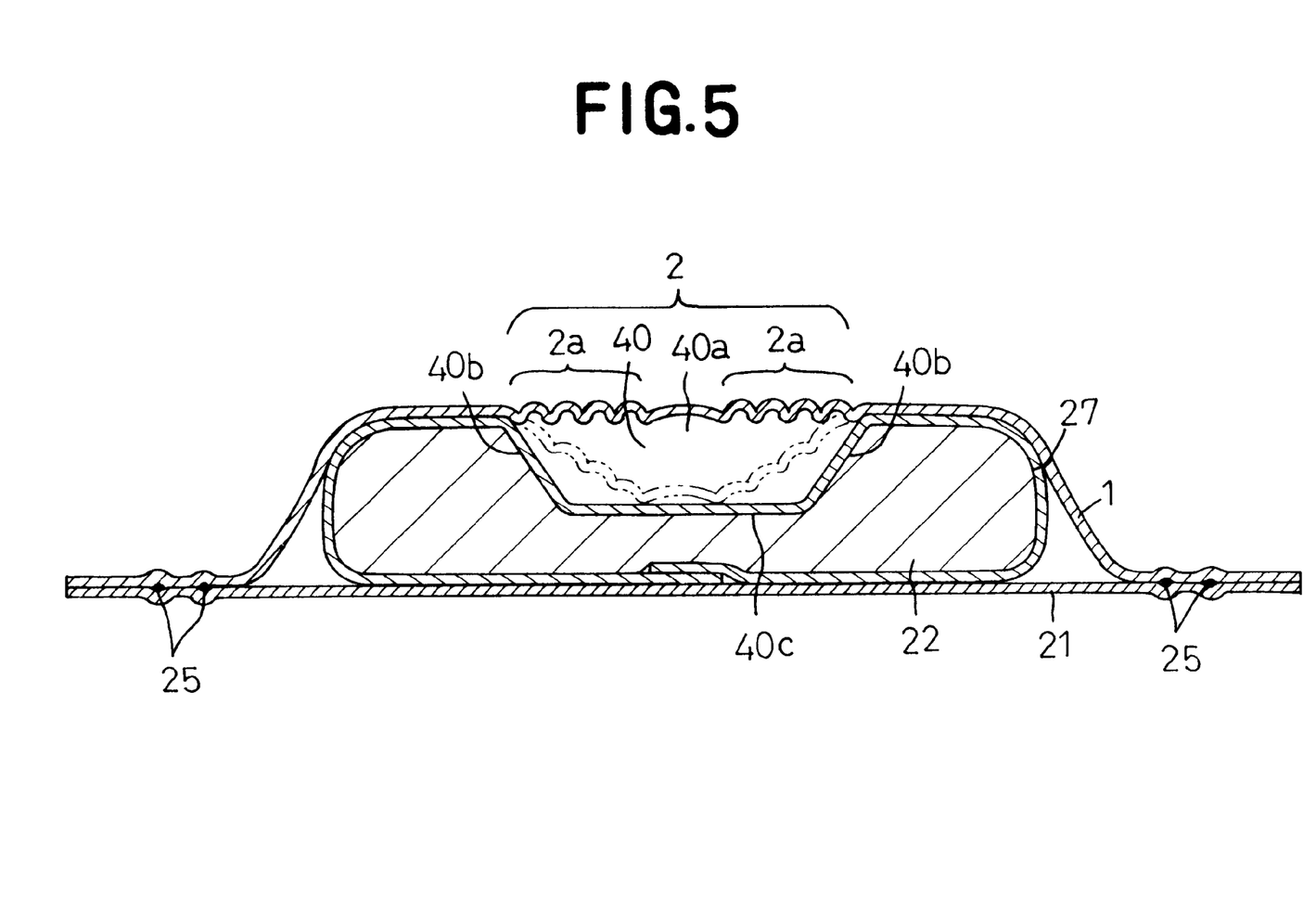
FIG. 5 is a sectional view taken along line B—B in FIG. 4.

FIG. 4 is a partially cutaway perspective view showing a disposable diaper using the sheet 1 of FIG. 1 and FIG. 5 is a sectional view taken along line B—B in FIG. 4. Referring to FIG. 4, imaginary lines indicate the diaper as the topsheet 1 is stretched or deformed downward with respect to the diaper. The diaper comprises a laminated panel 20 comprising the liquid-pervious topsheet 1, a liquid-impervious backsheet 21 and a liquid-absorbent core 22 disposed between the topsheet 1 and the backsheet 21 and joined to the inner surface of at least one of these two sheets 1, 21. The topsheet may be joined only at a peripheral region of the panel 20 to the core 22 and/or the backsheet 21 so that a central region including stretchable region 2 may be floated upward form the core 22.

The panel 20 has a front waist region 30, a rear waist region 32, a crotch region 31 extending between the front and rear waist regions 30, 32 as viewed longitudinally of the panel 20, opposite side edges 20a extending longitudinally of the panel 20 and curved inward transversely of the panel 20 in the crotch region 31, and opposite ends 20b extending transversely of the panel 20.

The inner side of the panel 20 is formed at a location destined to be placed against the wearer's hip with a cylindrical depression 40 adapted to receive feces discharged from the wearer. The depression 40 is defined by correspondingly shaping the core 22 and has an upper opening 40a, a side wall 40b and a bottom wall 40c. A space is left between the topsheet 1 covering the upper opening 40a and the bottom wall 40c of the depression 40.

The topsheet 1 has, at the location corresponding to the depression 40, the stretchable region 2 adapted to be stretchable or deformed up- and downward with respect to the topsheet 1. The stretchable region 2 is formed by a plurality of circular pleats 2a undulating from the peripheral edge toward the central zone of the stretchable region 2. In the stretchable region 2, the circular pleats 2a have their circumferences progressively reduced toward the central zone and are coaxially arranged so that the outermost pleat 2a lies in the vicinity of the peripheral edge of the upper opening 40a and the innermost pleat 2a lies substantially in the central zone of the bottom wall 40c of the depression 40.

The front and rear waist regions 30, 32 of the panel 20 are provided along the opposite ends 20b of the panel 20 with transversely extending elastic members 23, 24 disposed between the topsheet 1 and the backsheet 21 and secured under tension to at least one of these two sheets 1, 21 so that the elastic members 23, 24 are associated with a waist-opening of the diaper. The panel 20 is further provided along the opposite side edges 20a with longitudinally extending elastic members 25 disposed between the topsheet 1 and the backsheet 21 and secured under tension to at least one of these two sheets 1, 21. The rear waist region 32 of the panel 20 is provided with a pair of tape fasteners 26 extending from the opposite side edges 20a of the panel 20 inward transversely of the panel 20. The tape fasteners 26 having their proximal ends fixed to the side edges 20a.

The topsheet 1 and the backsheet 21 are joined together along their portions transversely extending beyond transversely opposite side edges of the core 22 as well as along their portions longitudinally extending beyond longitudinally opposite ends of the core 22.

The pleats 2a of the topsheet 1 are stretched or deformed under a weight of feces as feces is discharged onto the stretchable region 2 which is, in turn, stretched or deformed downward with respect to the panel 20 until the stretchable region 2 comes in contact with the side wall 40b and the bottom wall 40c of the core 22. The pleats 2a are coaxially arranged and therefore a substantially central zone of the stretchable region 2 comes in contact with the bottom wall 40c of the depression 40. In other words, the stretchable region 2 can be depressed in conformity with the shape of the depression 40 and thereby feces can be reliably received by the depression 40. Before feces is discharged, the stretchable region 2 of the topsheet 1 is maintained in contact with the wearer's hip and thereby alleviates a feeling of discomfort possibly experienced by the wearer due to the peripheral edge defining the upper opening 40a of the depression 40 coming in contact with the wearer's skin. It is possible to use the topsheet 1 of which the stretchable region 2 is formed by a spiral pleat 2a undulating from the peripheral edge toward the central zone of the stretchable region 2, as shown in FIG. 3.

The depression 40 adapted to receive feces may be tapered from the bottom wall 40c toward the upper opening 40a of the depression 40 or from the upper opening 40a toward the bottom wall 40c of the depression 40.

Figure 6:
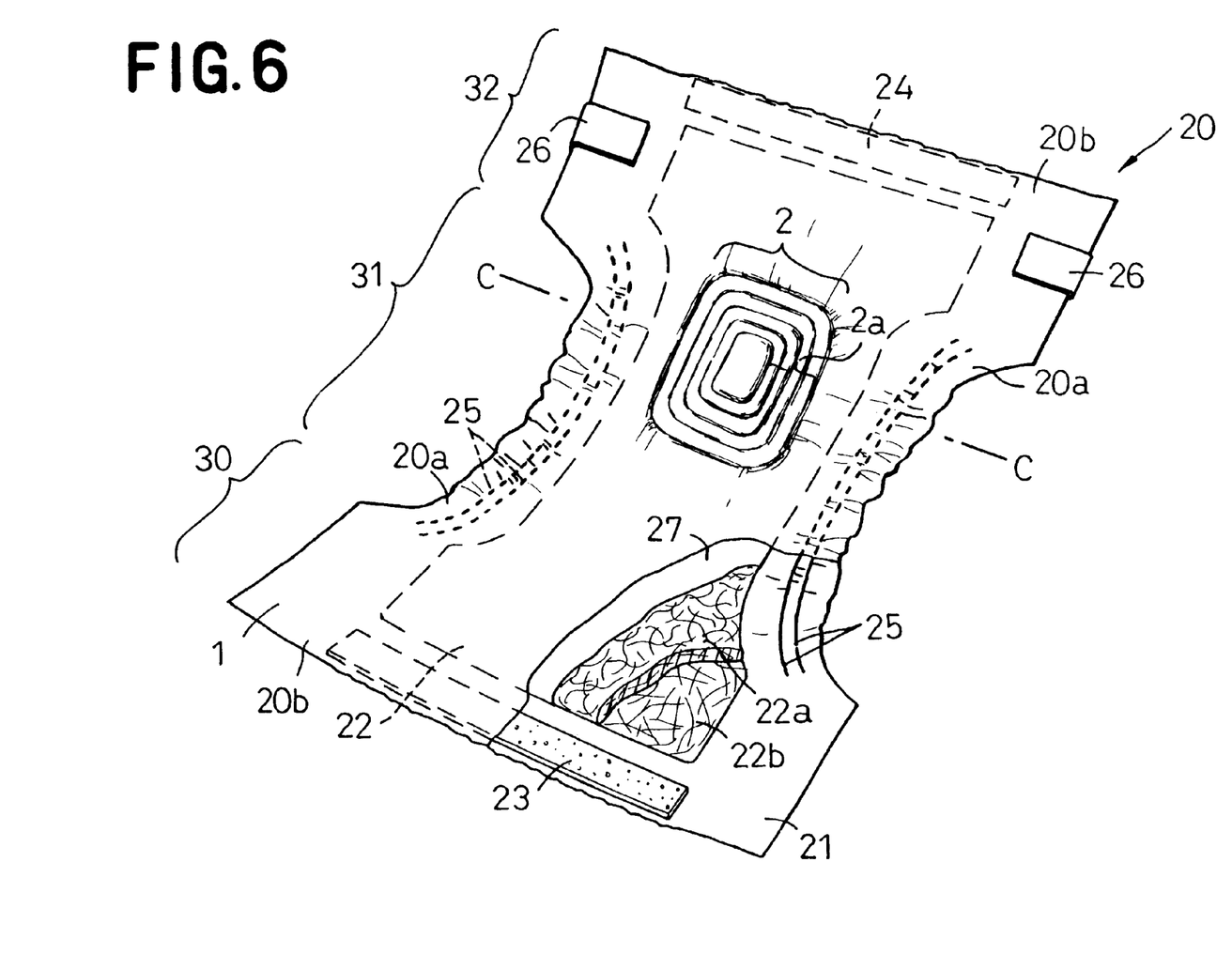
FIG. 6 is a view similar to FIG. 4 but showing another embodiment of the disposable diaper as partially broken away.
Figure 7:
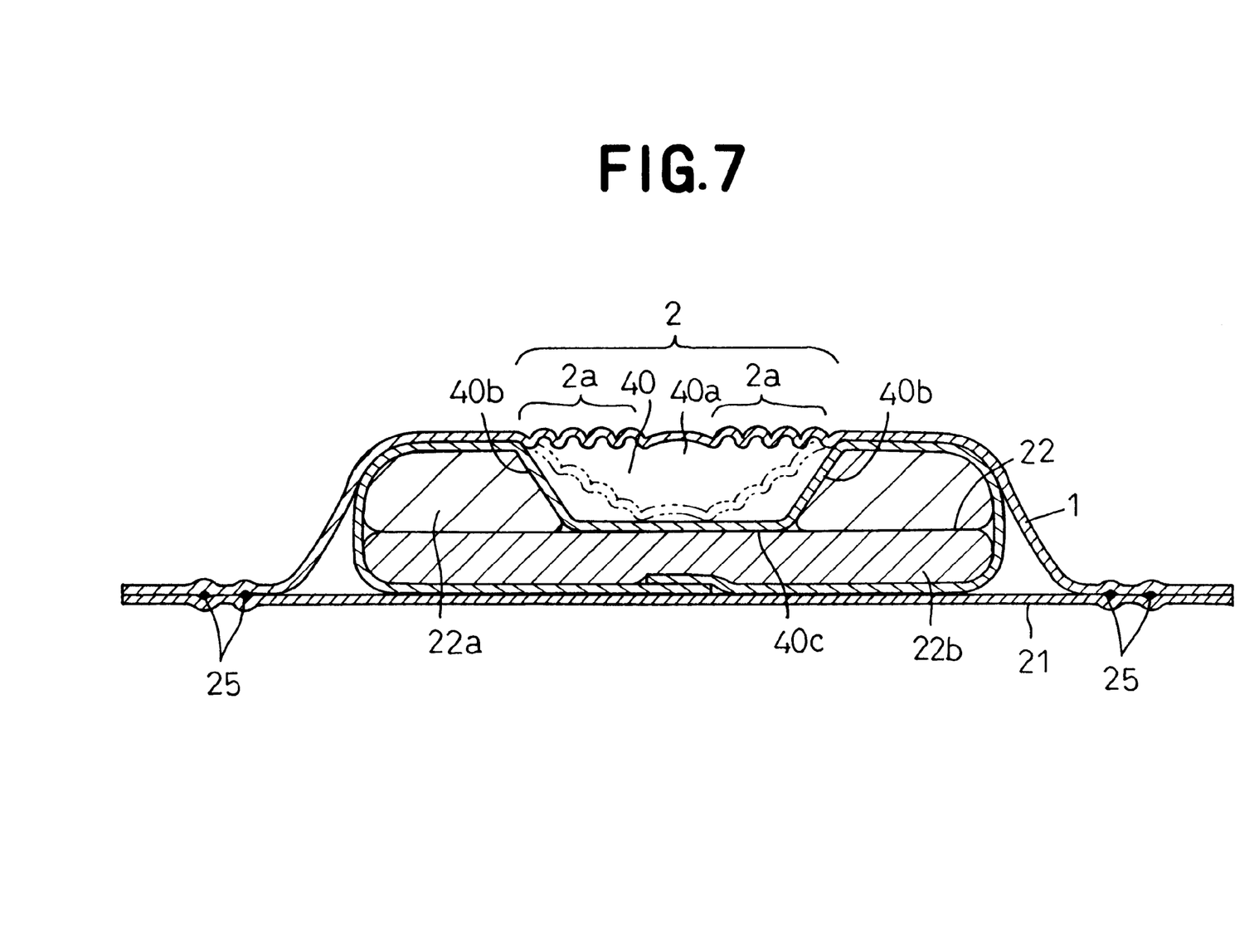
FIG. 7 is a sectional view taken along a line C—C in FIG. 6.

FIG. 6 is a view similar to FIG. 4 but showing another embodiment of the disposable diaper and FIG. 7 is a sectional view taken along line C—C in FIG. 6, where components similar to those previously described have the same reference numeral. The laminated panel 20 according to this embodiment is similar to that of FIGS. 4 and 5 except for that the stretchable region 2 is formed by a plurality of round cornered rectangular pleats 2a and the depression 40 is defined by covering a through-hole formed in an upper layer core 22a substantially in its central zone with a lower layer core 22b. Accordingly, the description of the remaining portions of the laminated panel 20 according to this embodiment is omitted.

Japanese Utility Model Application Disclosure No. 1994-21624 describes a disposable diaper comprising a liquid-pervious topsheet, a liquid-impervious backsheet and a liquid-absorbent core disposed between these two sheets wherein the core is formed at its zone corresponding to the wearer's hip with a depression adapted to receive feces and the topsheet partially extending downward from an upper peripheral edge along a side wall of the depression is joined to the side wall and a bottom wall. Japanese Patent Application Disclosure No. 1996-191857 also describes a disposable diaper comprising a liquid-pervious topsheet, a liquid-impervious backsheet and a liquid-absorbent core disposed between these two sheets wherein the diaper is formed at its zone corresponding to the wearer's hip with a depression defined by an upper layer core having a through-hole and a lower layer core covering the through-hole from below to receive feces and the topsheet partially extending downward from an upper peripheral edge of the depression along its side wall is fixed to said side wall and a bottom wall of said depression.

Both of the diapers respectively described in the Japanese Utility Model Application Disclosure No. 1994-21624 and Japanese Patent Application Disclosure No. 1996-191857 disadvantageously require a step of joining the topsheet to the side wall and the bottom wall of the core's depression in the process for making these diapers. On the contrary, it is unnecessary for the diaper of the invention illustrated by FIGS. 4, 6 to join the topsheet to the side wall and the bottom wall of the core's depression in the course of covering the upper surface of the core with the topsheet. Accordingly, the steps of process for making the diaper can be partially eliminated.

The backsheet 21 is made of a synthetic resin film or a laminated sheet consisting of a synthetic resin film and a hydrophobic nonwoven fabric. The core 22 comprises a mixture of fluff pulp and highly absorptive polymer particles or such mixture added with suitable fiber serving to hold a core's shape. The mixture is compressed to a desired thickness and entirely covered with a liquid-pervious sheet such as tissue paper. Fixing and joining of various members may be performed using suitable adhesive agent such as hot melt adhesive agent or sealing technique such as heat-sealing or sonic-sealing.

The topsheet of FIGS. 1, 3 and 4 may be used in the diaper other than the diaper illustrated in FIGS. 4 and 6 so far as the diaper has the depression adapted to receive feces. The diapers having such depressions adapted to receive feces other than the diaper of FIGS. 4 and 6 are described in Japanese Utility Model Application Disclosure No. 1993-86320, Japanese Utility Model Application Disclosure No. 1994-5614 and Japanese Patent Application Disclosure Gazette No. 1996-196565.

The disposable absorbent article according to this invention enables it to form the topsheet at a desired location with a region which is stretchable or deformable up- and downward with respect to the upper and lower surfaces so that the topsheet may be formed in this region with a concave or a convex as said region is stretched. The topsheet according to this invention is free from any apprehension that a plurality of fine gathers might be formed in the stretchable region and give the wearer a feeling of discomfort.

What is claimed is:

1. A disposable absorbent article comprising:

a liquid-permeable topsheet;

a liquid-impermeable backsheet;

a liquid-absorbent core disposed therebetween; and said topsheet being provided at a predetermined location on upper and lower surfaces thereof with a stretchable region adapted to be stretchable up- and downward with respect to said upper and lower surfaces, said stretchable region being formed by a plurality of pleats which undulate from a peripheral edge toward a central zone of said stretchable region and which are in the form of regression lines that are coaxially arranged.

2. The article according to claim 1, wherein said article has a front waist region, a rear waist region and a crotch region extending between said front and rear waist regions, said stretchable region being provided in said crotch region.

3. The article according to claim 1, wherein regression lines are at least one of circular and square ones.

4. The article of claim 1, wherein a portion of the plurality of pleats extend into the central zone of the stretchable region.

5. A disposable absorbent article comprising:

a liquid-permeable topsheet;

a liquid-impermeable backsheet;

a liquid-absorbent core disposed therebetween; and said topsheet being provided at a predetermined location on upper and lower surfaces thereof with a stretchable region adapted to be stretchable up- and downward with respect to said upper and lower surfaces, said stretchable region being formed by a plurality of pleats which undulate from a peripheral edge toward a central zone of said stretchable region and are in the form of a spiral line.

6. The article according to claim 5, wherein said article has a front waist region, a rear waist region and a crotch region extending between said front and rear waist regions, said stretchable region being provided in said crotch region.

7. The article of claim 5, wherein a portion of the plurality of pleats extend into the central zone of the stretchable region.

8. A disposable absorbent article comprising:

a liquid-permeable topsheet;

a liquid-impermeable backsheet;

a liquid-absorbent core disposed therebetween;

said topsheet being provided at a predetermined location on upper and lower surfaces thereof with a stretchable region adapted to be stretchable up- and downward with respect to said upper and lower surfaces, said stretchable region being formed by a plurality of pleats which undulate from a peripheral edge toward a central zone of said stretchable region; and said core being formed with a depression adapted to receive feces discharged from the wearer, said depression having an upper opening, a side wall and a bottom, said stretchable region being located over said upper opening.

9. The article according to claim 8, wherein said article has a front waist region, a rear waist region and a crotch region extending between said front and rear waist regions, said stretchable region being provided in said crotch region.

10. The article of claim 8, wherein a portion of the plurality of pleats extend into the central zone of the stretchable region.

* * * * *